(12) United States Patent
Lin et al.

(10) Patent No.: US 11,193,933 B2
(45) Date of Patent: Dec. 7, 2021

(54) MEASURING GAPDH PROTEIN FOR DIAGNOSIS AND TREATMENT OF ALZHEIMER'S DISEASE

(71) Applicant: Dr. Power Stem Biomedical Research Inc., Ltd., Yilan (TW)

(72) Inventors: Chai-Ching Lin, Yilan County (TW); Chen-Wei Tsai, Taipei (TW)

(73) Assignee: DR. POWER STEM BIOMEDICAL RESEARCH INC., LTD., Yilan (TW)

( * ) Notice: Subject to any disclaimer, the term of this patent is extended or adjusted under 35 U.S.C. 154(b) by 0 days.

(21) Appl. No.: 15/335,036

(22) Filed: Oct. 26, 2016

(65) Prior Publication Data
US 2018/0113129 A1  Apr. 26, 2018

(51) Int. Cl.
*G01N 33/573* (2006.01)

(52) U.S. Cl.
CPC .... *G01N 33/573* (2013.01); *C12Y 102/01012* (2013.01); *G01N 2333/90203* (2013.01); *G01N 2800/2821* (2013.01); *G01N 2800/50* (2013.01)

(58) Field of Classification Search
CPC ......... G01N 33/573; G01N 2800/2821; G01N 2333/90203; G01N 2800/50; G01N 33/6896; C12Y 102/01012
See application file for complete search history.

(56) References Cited

U.S. PATENT DOCUMENTS

| | | |
|---|---|---|
| 2002/0172676 A1 | 11/2002 | Jackowski et al. |
| 2004/0265849 A1 | 12/2004 | Cargill et al. |

FOREIGN PATENT DOCUMENTS

| | | |
|---|---|---|
| WO | WO 02/093174 A2 | 11/2002 |
| WO | WO 2006/020269 A2 | 2/2006 |

OTHER PUBLICATIONS

Vickers. A vaccine against Alzheimer's disease: developments to date. Drugs Aging 2002; 19(7):487-94.*
Perrin et al. Multimodal techniques for diagnosis and prognosis of Alzheimer's disease. Nature Oct. 15, 2009;461(7266):916-22, Published online Oct. 14, 2009.*
Hampel et al. The future of Alzheimer's disease: the next 10 years. Prog Neurobiol. Dec. 2011;95(4):718-28. Epub Nov. 22, 2011.*
Butterfield et al. Oxidatively modified glyceraldehyde-3-phosphate dehydrogenase (GAPDH) and Alzheimer's disease: many pathways to neurodegeneration. J Alzheimers Dis. 2010;20(2):369-93.*
Kadmiri et al. Glyceraldehyde-3-phosphate dehydrogenase (GAPDH) and Alzheimer's disease.Pathol Biol (Paris). Dec. 2014;62(6): 333-6. Epub Sep. 22, 2014.*
"Enzyme-linked Immunosorbent Assay Kit For Glyceraldehyde-3-Phosphate Dehydrogenase (GAPDH)," Cloud-Clone Corp., Jul. 2013.
El Kadmiri, N., et al, "Glyceraldehyde-3-phosphate dehydrogenase (GAPDH) and Alzheimer's disease," Pathologie Biologie, Dec. 2014, vol. 62, No. 6, pp. 333-336.
European Search Report for Appl. No. 16194973.0 dated Feb. 21, 2017.
Sultana, R., et al., "Identification of nitrated proteins in Alzheimer's desease brain using a redox proteomics approach," Neurobiol. Dis., 2006, vol. 22, pp. 76-87.
Sunaga, K., et al, "Glyceraldehyde-3-phosphate dehydrogenase is over-expressed during apoptotic death of neuronal cultures and is recognized by a monoclonal antibody against amyloid plaques from Alzheimer's brain," Neuroscience Letters, 1995, vol. 200, pp. 133-136.
Wang, Q., et al, "Proteomic analysis of neurofibrillary tangles in Alzheimer disease identifies GAPDH as a detergent-insoluble paired helical filament tau binding protein," The FASEB Journal, Feb. 23, 2005, pp. 1-12.

* cited by examiner

*Primary Examiner* — Gregory S Emch
(74) *Attorney, Agent, or Firm* — Birch, Stewart, Kolasch & Birch, LLP

(57) ABSTRACT

The present invention is related to a method for risk detection, diagnosis, prognosis and monitoring of Alzheimer's disease (AD). The method comprises the steps of: (1) measuring the level of glyceraldehyde 3-phosphate dehydrogenase (GAPDH) in a sample from the subject, and (2) comparing the level of GAPDH in the sample with two or more AD reference levels of GAPDH.

1 Claim, 3 Drawing Sheets

MEASURING GAPDH PROTEIN FOR DIAGNOSIS AND TREATMENT OF ALZHEIMER'S DISEASE

FIELD OF THE INVENTION

The present invention generally relates to a method for risk detection, diagnosis, prognosis and monitoring of Alzheimer's disease (AD).

BACKGROUND OF THE INVENTION

Alzheimer's disease (AD) is the most common form of dementia. Alzheimer's disease is classified as a neurodegenerative disorder, the cause and progression of which are poorly understood. The disease process appears to be associated with plaques and tangles in the brain. The most common early symptom is short term memory loss—difficulty in remembering recent events.

Until now, there are no standard diagnostic tests for AD, so the diagnosis rests on the clinical information provided by the AD patients and the findings of the neurological examination. Usually, the diagnosis of AD is confirmed by the tests for evaluating a patient's behavior and thinking abilities, often followed by a brain scan if available. However, an examination of brain tissue is required for a conclusive diagnosis. The traditional methods to assess AD are non-specific or expensive, including, for example, the Mini Mental State Examination (MMSE), which is a psychometric test in the form of a Functional Assessment Questionnaire (FAQ) to examine the scale for functional autonomy (Tombaugh, The mini-mental state examination: a comprehensive review. *J. Am. Geriatr. Soc.* 40, 922-935, 1992); the invasive tests of tau and amyloid-β concentrations in cerebrospinal fluid (Wang et al., Proteomic analysis of neurofibrillary tangles in Alzheimer disease identifies GAPDH as a detergent-insoluble paired helical filament tau binding protein. *FASEB J.* 19, 869-871, 2005); a neuroimaging, particularly a computed tomography (CT), which is very expensive (Haydel et al., Indications for computed tomography in patients with minor head injury. *N. Engl. J. Med.* 343, 100-105, 2000).

WO2013153461 discloses methods by specific biomarkers in saliva for risk detection, diagnosis, prognosis and monitoring of Alzheimer's and Parkinson's diseases, wherein the salivary biomarkers comprise two or more of cTnI, myoglobin, MMP-9, MMP-8, MMP-2, sICAM-1, myeloperoxidase [MPO], IL-4, and/or IL-5; B-type natiuretic peptide [BNP], IL-1a, IL-11, IL-10, TNF-α, IFN-γ, VEGF, insulin, GLP-1 (active), GLP-1 (total), TREM1, Leukotriene E4, Akt1, Aβ-40, Aβ-42, Fas ligand, PSA, G-CSF, MIP-1a, IL-22, IL-8, IL-21, IL-15, IL-6, IL-7, GM-CSF, IL-2, IL-12, IL-17a, IL-Iβ, MCP, IL-32 or RANTES, apolipoproteins A1, D and E, ischemia-modified albumin (IMA), fibronectin, s. alpha-amylase, aspartate aminotransferase, lactate dehydrogenase, tissue factor activity, MCP-1, sVCAM-1, sCD-40, insulin-like growth factor I (IGF-I), and IGF-II.

U.S. Pat. No. 9,012,237 discloses a method for diagnosing of Alzheimer's disease, or determining the risk of developing Alzheimer's disease in a subject by measuring specific biomarkers, wherein the biomarkers are at least four biomarkers selected from brain-derived neurotrophic factor (BDNF), insulin-like growth factor-1 (IGF-1), tumor growth factor beta 1 (TGF-beta 1), vascular endothelial growth factor (VEGF), interleukin 18 (IL-18), and monocyte chemotactic protein-1 (MCP-1), and whereby an increase of IL-18, and/or MCP-1, and/or the decrease of BDNF, IGF-1, VEGF and/or TGF-beta 1 is indicative for the presence or risk of development of AD.

It is still desired to develop a much easier method for diagnosis of AD and determination of the AD risk.

SUMMARY OF THE INVENTION

It is unexpectedly discovered in this invention that the level of glyceraldehyde 3-phosphate dehydrogenase (GAPDH) in a sample from an AD patient can serve as a single biomarker for diagnosis or risk detection of Alzheimer's disease.

Accordingly, in one aspect, the present invention provides a method for diagnosis of Alzheimer's disease (AD) or detection of AD risk in a subject, comprising the steps of:
(1) taking samples from a baseline set of subjects, wherein the baseline set of subjects comprises a control group having subjects without AD and AD group with subjects that have different stages and types of Alzheimer's disease;
(2) measuring baseline levels of a baseline set of glyceraldehyde 3-phosphate dehydrogenase (GAPDH) as a single biomarker in the baseline samples;
(3) determining AD reference levels for GAPDH in the test set based on the baseline levels of GAPDH in the test set;
(4) measuring a test sample for levels of GAPDH; and
(5) determining the test sample is positive or risk for AD if the level of GAPDH in the test sample is higher than the AD references levels as determined in step (3).

In one embodiment of the present invention, the sample is a blood, urine, or saliva sample. In a specific embodiment, the sample is a plasma sample.

In one embodiment of the invention, the AD reference levels for GAPDH are between about 380 ng/dL and about 720 ng/dL; wherein the level of GAPDH in a test sample from the subject being higher than about 720 ng/dL indicates a diagnosis of Alzheimer's disease; while the level of GAPDH in a test sample from the subject being less than about 380 ng/dL indicates a diagnosis of a low risk for Alzheimer's disease; and the level of GAPDH in a test sample from the subject being between about 380 ng/dL and about 720 ng/dL indicates a diagnosis of a high risk for Alzheimer's disease.

In the present invention, the level of GAPDH is determined by an enzyme-linked immunosorbent assay (ELISA) kit.

In another aspect, the invention provides a method to test for positive or risk for Alzheimer's disease (AD) in a subject in need thereof, comprising the steps of:
(1) measuring the level of glyceraldehyde 3-phosphate dehydrogenase (GAPDH) in a plasma sample from the subject, and
(2) comparing the level of GAPDH in the sample from the subject with one or more AD reference levels for GAPDH of about 380 ng/dL and about 720 ng/dL; and
(3) determining the sample is positive or risk for AD if the level of GAPDH in the sample is higher than the AD references levels for GAPDH.

In one embodiment of the invention, the sample is a plasma sample.

In one particular embodiment of the invention, the AD references levels for GAPDH are between about 380 ng/dL and about 720 ng/dL, wherein the level of GAPDH in a sample from the subject being higher than about 720 ng/dL indicates a diagnosis of Alzheimer's disease; while the level of GAPDH in a sample from the subject being less than about 380 ng/dL indicates a diagnosis of a low risk for Alzheimer's disease; and the level of GAPDH in a sample from the subject being between about 380 ng/dL and about 720 ng/dL indicates a diagnosis of a high risk for Alzheimer's disease.

In one further aspect, the invention provides a test kit for performing the method of the invention to test for positive or risk for Alzheimer's disease (AD) comprising:
a plurality of test devices, each configured to produce a signal level proportional to a level present on the test device of GAPDH; and
a reader configured to read the levels of GAPDH on the test devices.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The foregoing summary, as well as the following detailed description of the invention, will be better understood when read in conjunction with the appended drawing. In the drawings.

DESCRIPTION OF THE INVENTION

Figure 1:
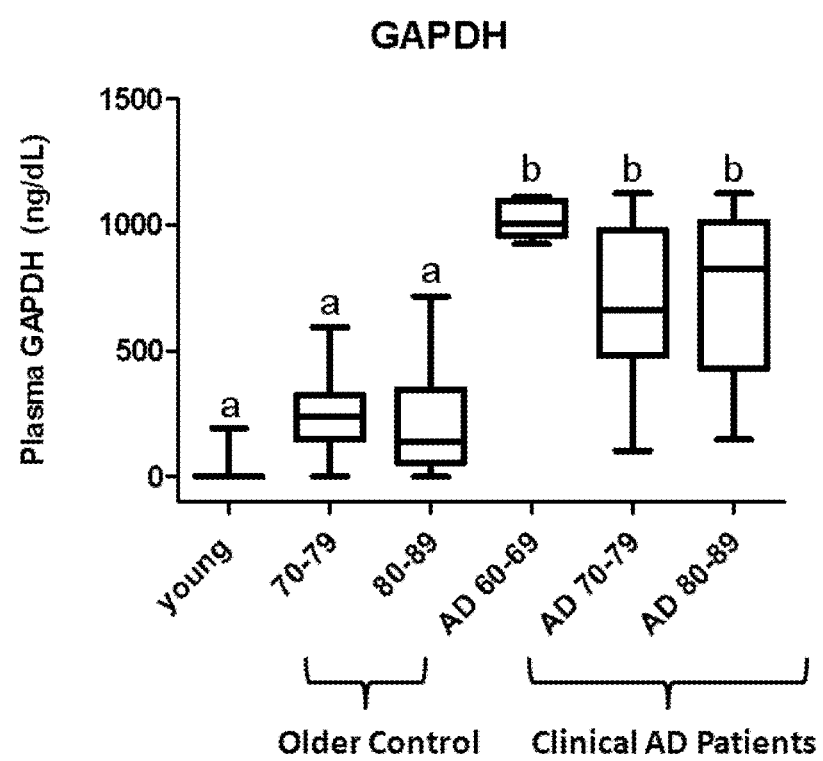
FIG. 1 shows the levels of GAPDH in plasma samples of the control and AD subjects, wherein data were presented as the box from the lower quartile to the upper quartile; the median is drawn parallel in the box; the whiskers stretch out from half-way up the sides of the box to the minimum and the maximum; different letters in the same box indicates a significant difference (P<0.05).

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

The present invention provides a method for diagnosis of Alzheimer's disease (AD) by determining the level of glyceraldehyde 3-phosphate dehydrogenase (GAPDH) in a sample from a subject in need thereof.

The term "diagnosis" or "diagnosing" as used herein refers to assessing whether a subject suffers from a disease or not, i.e., Alzheimer's disease in the present invention. As will be understood by those skilled in the art, such an assessment, although preferred to be, may not be correct for 100% of the investigated subjects. The term, however, requires that a statistically significant portion of subjects can be correctly assessed and, thus, diagnosed. The term includes individual diagnosis of Alzheimer's disease or its symptoms as well as continuous monitoring of a subject. Monitoring, i.e. diagnosing a subject with or without Alzheimer's disease or the symptoms accompanying it at various time points or age, includes monitoring of a subject known to suffer from Alzheimer's disease as well as monitoring of a subject known to be a risk of developing Alzheimer's disease. Furthermore, monitoring can also be used to determine whether a subject is treated successfully or whether at least symptoms of Alzheimer's disease can be ameliorated over time by a certain therapy.

Glyceraldehyde-3-phosphate dehydrogenase (GAPDH) were identified as the targets of nitration in AD hippocampus, and the oxidative dysfunction of GAPDH may significantly contribute to loss of neuronal function and neurodegeneration in AD brain. (Sultana et al., Identification of nitrated proteins in Alzheimer's disease brain using a redox proteomics approach. *Neurobiol. Dis.* 22, 76-87, 2006.) It was also reported that GAPDH plays a critical role in neurodegeneration (Petrak et al., Deja vu in proteomics. A hit parade of repeatedly identified differentially expressed proteins. *Proteomics* 8, 1744-1749, 2008; Piechaczyk et al., Unusual abundance of vertebrate 3-phosphate dehydrogenase pseudogenes. *Nature* 312, 469-471, 1984). However, there is no method for diagnosis of AD through the determination of the levels of GAPDH until now.

In the present invention, the level of GAPDH in a sample from the subject can be determined by any known or conventional method/kit for measuring GAPDH. In one embodiment of the invention, a kit using an antibody that specifically binds to GAPDH can be used, for example, an enzyme-linked immunosorbent assay (ELISA) kit.

The term "biomarker" as used herein refers to a molecular species which serves as an indicator for a disease or effect as referred to in this specification. Said molecular species can be, but is not limited to a nucleotide sequence, an amino acid sequence, DNA, a protein, or a metabolite which is found in a sample of a subject.

As used herein, the term "subject" or "subject in need thereof" refers to a mammal, preferably a human being, male or female, at any age, regardless of having Alzheimer's disease or not.

The term "antibody" refers to whole antibodies, their derivatives or functional fragments thereof which still retain their binding specificity. In particular, the antibody in the invention that specifically binds to GAPDH.

As used herein, the term "sample" refers to a sample obtained from a subject to be investigated, including, for example, a blood, urine, saliva and tissue fluid sample.

According to the present invention, the method for diagnosis of Alzheimer's disease (AD) or detection of AD risk in a subject, comprising the steps of:
(1) taking samples from a baseline set of subjects, wherein the baseline set of subjects comprises a control group having subjects without AD and AD group with subjects that have different stages and types of Alzheimer's disease;
(2) measuring baseline levels of a baseline set of glyceraldehyde 3-phosphate dehydrogenase (GAPDH) as a single biomarker in the baseline samples;
(3) determining one or more AD reference levels for GAPDH in the test set based on the baseline levels of GAPDH in the test set;
(4) measuring a test sample for levels of GAPDH; and (5) determining the test sample is positive or risk for AD if the level of GAPDH in the test sample is higher than the AD references levels as determined in step (3).

According to the present invention, the sample may be a blood, urine, saliva or any physiological sample. In one particular embodiment, the sample is a blood sample, especially a plasma sample.

On the other hand, the present invention provides a method to test for positive or risk for Alzheimer's disease (AD) in a subject in need thereof, comprising the steps of:
(1) measuring the level of glyceraldehyde 3-phosphate dehydrogenase (GAPDH) in a sample from the subject, and
(2) comparing the level of GAPDH in the sample from the subject with one or more AD reference levels for GAPDH; and
(3) determining the sample is positive or risk for AD if the level of GAPDH in the sample is higher than the AD references levels for GAPDH.

In the present invention, the level of GAPDH may be determined by a kit using an antibody that specifically binds to GAPDH. As illustrated in the example below, the levels of GAPDH are determined by an enzyme-linked immunosorbent assay (ELISA) kit, and the AD reference levels for GAPDH are determined according to the statistic data of specificity data (%) and the GAPDH levels of samples from all subjects, particularly by a regression analysis of the specificity data and the GAPDH levels.

As shown in the example, the AD reference levels for GAPDH are between about 380 ng/dL and about 720 ng/dL; wherein the level of GAPDH in a test sample from the subject being higher than about 720 ng/dL indicates a diagnosis of Alzheimer's disease; while the level of GAPDH in a test sample from the subject being less than about 380 ng/dL indicates a diagnosis of a low risk for Alzheimer's disease; and the level of GAPDH in a test sample from the subject being between about 380 ng/dL and about 720 ng/dL indicates a diagnosis of a high risk for Alzheimer's disease. It is confirmed in the example that the level of GAPDH can be used as a single biomarker for diagnosis or risk detection of Alzheimer's disease.

The present invention is further illustrated by the following examples, which are provided for the purpose of demonstration rather than limitation.

EXAMPLES

I. Materials and Methods
1. Subjects

A total of 43 AD patients at the age of 60-69 (n=5, male 3, female 2), 70-79 (n=18, male -9, female 9) and 80-89 (n=20, male 10, female 10), and 37 older controls at the age of 70-79 (n=20, male 11, female 9) and 80-89 (n=17, male 13, female 4) were recruited from the outpatient of the Memory Clinic of Taipei Veterans General Hospital (TVGH). Diagnostic determinations of AD patients based on the results of clinical interviews, physical examinations, laboratory findings and image investigations (CT and/or MRI) were made at a clinical consensus meeting. An AD diagnosis was made according to the criteria of National Institute of Neurological and Communicative Disorders and Stroke—Alzheimer's Disease and Related Disorders Association (NINCDS-ADRDA) (Froese, Cube law, condition factor and weight-length relationships: history, meta-analysis and recommendations. *J. Appl. Ichthyol.* 22, 241-253, 2006). All AD patients received neurological examinations, laboratory tests, and neuroimaging evaluation as diagnostic surveys. Older controls were volunteers without cognitive complaints, who were recruited from outpatient clinics. Also, the 16 young people at the age of 20-29 (n=16, male 8, female 8) recruited were volunteers from the National Ilan University campus.

2. Samples

Human plasma samples were collected by the containing EDTA-2Na plastic syringe and then centrifuged at 4° C., 3000 rpm, and 30 minutes to obtain the protein supernatant. The plasma proteins were dropped into the liquid nitrogen and then kept frozen at −80° C. for the following analysis. The Enzyme-Linked Immunosorbent Assay (ELISA) was used to quantify the specific protein level in the plasma. The commercial reagents were purchased from the human GAPDH ELISA Kit (DuoSet IC® DYC5718, R&D Systems, USA). The protocols to use the kits were followed by their directions. The samples were analyzed by the ELISA reader (SpectraMax® M2 Microplate Reader, Molecular Devices Inc., California, USA) at the 450 nm of wavelength.

3. GAPDH Levels Assay

The plasma GAPDH levels from the ELISA quantification were subjected to the nonparametric Kruskal-Wallis test (GraphPad Prism® Version 5.01, © 1992-2007 GraphPad Software Inc.). Data were presented as the box from the lower quartile to the upper quartile. The median is drawn parallel in the box. The whiskers stretch out from half-way up the sides of the box to the minimum and the maximum. Next, we use the ROC curve statistical methods (MedCalc® Version 13.3.1.0, © 1993-2014 MedCalc Software bvba) to identify the associated criterion of high AD risk from the plasma GAPDH and natural aging from the plasma Cyt C1, respectively. The area under the ROC curve (AUC) is possibly located between 1.0 and 0.5. The AUC has lower accuracy from 0.5 to 0.7, some accuracy from 0.7 to 0.9, and high accuracy above 0.9. When AUC=0.5, it indicates that the diagnostic method is completely ineffective, no diagnostic value. AUC<0.5 does not meet the real situation rarely occurs in practice.

Statistical Analysis

Comparisons between two groups were analyzed by Student's t-test. Comparisons within three groups were analyzed by ANOVA test. Comparison of patient survival curve was analyzed by Log-rank test. Comparison of in vivo tumourigeneicity was analyzed by Fisher's exact test. A value of $P<0.05$ was considered statistically significant.

II. Results

The human plasma samples were collected from young controls at the age of 20-29 (n=16, male 8, female 8), older controls at the age of 70-79 (n=20, male 11, female 9) and 80-89 (n=17, male 13, female 4), and AD patients at the age of 60-69 (n=5, male 3, female 2), 70-79 (n=18, male 9, female 9) and 80-89 (n=20, male 10, female 10). The data was subjected to the nonparametric Kruskal-Wallis test using the GraphPad prism pack module.

The plasma GADPH of the control group, irrespectively of age and sex, was all significantly lower than those of AD patients ($P<0.05$), see FIG. 1, based on the box-and-whisker plot. All the data as collected are shown in Table 1.

As shown in Table 1, the criterion >718 ng/dL of plasma GAPDH showed 100% specificity to AD. When the level of plasma GAPDH was located in the range from 0 to 378 ng/dL, it indicated low risk of AD condition. The border line for the criterion of association to AD was found to be a 378 ng/dL level of plasma GAPDH. In addition, high risk of AD condition (>90% specificity) was determined to be where the level of plasma GAPDH was between 378.7 and 718 ng/dL. Where the plasma GAPDH level was as high as 718 ng/dL, 100% confident diagnosis was decided for specific AD.

After the statistical analysis of the ROC, the method has been proven to be highly accurate to assess the condition of AD.

TABLE 1

The correlation between plasma GAPDH level and AD risk

| Criterion | Sensitivity | 95% CI | Specificity | 95% CI | AD risk |
|---|---|---|---|---|---|
| ≥0 | 100.00 | 91.8-100.0 | 0.00 | 0.0-6.7 | Low |
| >70.472 | 100.00 | 91.8-100.0 | 45.28 | 31.6-59.6 | Low |
| >103.6066 | 97.67 | 87.7-99.9 | 45.28 | 31.6-59.6 | Low |
| >144.2486 | 97.67 | 87.7-99.9 | 52.83 | 38.6-66.7 | Low |
| >147.0755 | 95.35 | 84.2-99.4 | 52.83 | 38.6-66.7 | Low |
| >251.6232 | 95.35 | 84.2-99.4 | 75.47 | 61.7-86.2 | Low |
| >273.3577 | 93.02 | 80.9-98.5 | 75.47 | 61.7-86.2 | Low |
| >316.1778 | 93.02 | 80.9-98.5 | 83.02 | 70.2-91.9 | Low |
| >337.0781 | 88.37 | 74.9-96.1 | 83.02 | 70.2-91.9 | Low |
| >338.1439 | 88.37 | 74.9-96.1 | 84.91 | 72.4-93.3 | Low |
| >347.4587 | 86.05 | 72.1-94.7 | 84.91 | 72.4-93.3 | Low |
| >378.7396 | 86.05 | 72.1-94.7 | 90.57 | 79.3-96.9 | High |
| >390.8812 | 83.72 | 69.3-93.2 | 90.57 | 79.3-96.9 | High |
| >446.6771 | 83.72 | 69.3-93.2 | 92.45 | 81.8-97.9 | High |
| >498.8583 | 74.42 | 58.8-86.5 | 92.45 | 81.8-97.9 | High |
| >521.3342 | 74.42 | 58.8-86.5 | 94.34 | 84.3-98.8 | High |
| >551.1322 | 69.77 | 53.9-82.8 | 94.34 | 84.3-98.8 | High |
| >579.6789 | 69.77 | 53.9-82.8 | 96.23 | 87.0-99.5 | High |
| >592.284 | 65.12 | 49.1-79.0 | 96.23 | 87.0-99.5 | High |
| >594.6474 | 65.12 | 49.1-9.0 | 98.11 | 89.9-100.0 | High |
| >702.3464 | 55.81 | 39.9-70.9 | 98.11 | 89.9-100.0 | High |
| >717.9637 | 55.81 | 39.9-70.9 | 100.00 | 93.3-100.0 | Yes |
| >1126.84 | 0.00 | 0.0-8.2 | 100.00 | 93.3-100.0 | Yes |

Figure 2A:
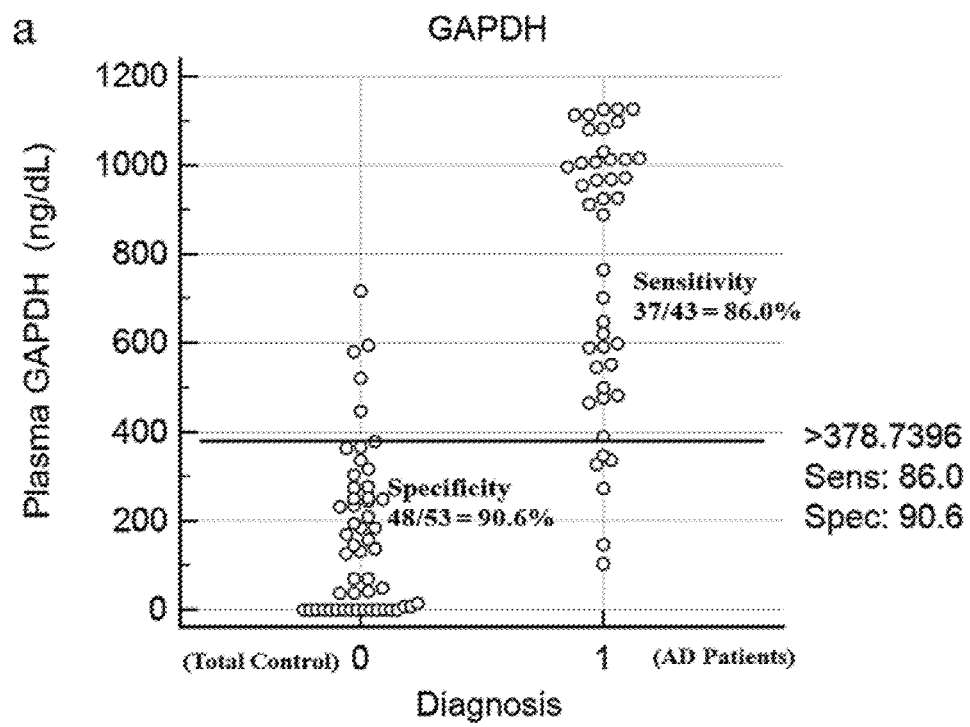
FIG. 2(A) shows that the associated criterion of AD is >378.74 ng/dL, wherein the designated diagnosis number of 0 and 1 indicates control without AD and AD subject, respectively.
Figure 2B:
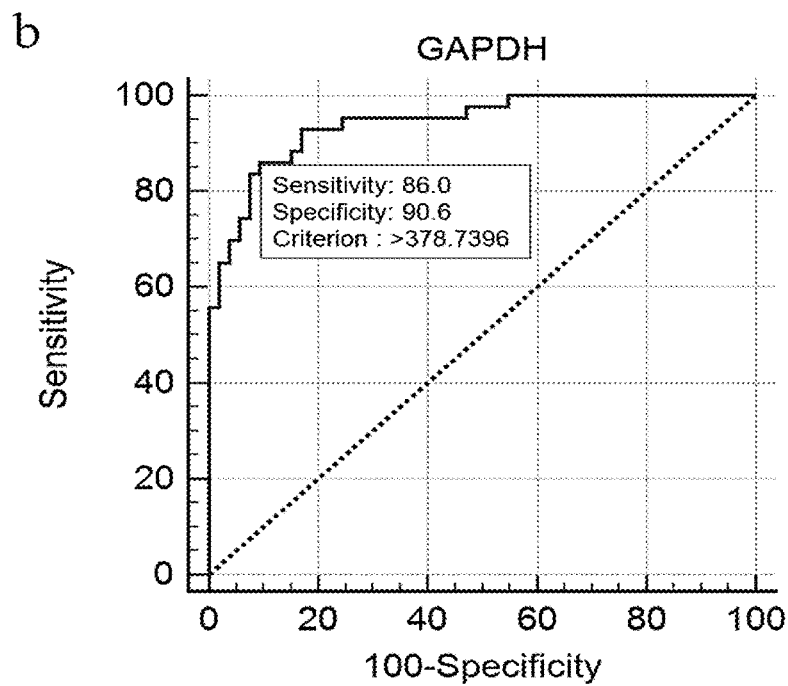
FIG. 2(B) shows that the area under the ROC curve (AUC) is 0.944±0.0219, indicating high accuracy; 0.877-0.981 of 95% confidence interval (CI) and 20.271 of z statistic (P<0.0001), is able to reach 86.4% sensitivity and 90.6% specificity.

Based on the statistical analysis of the ROC curve, the associated criterion of plasma GAPDH for AD was more than 378.74 ng/dL as shown in FIG. 2(A). The designated diagnosis number of 0 and 1 indicated the control group without AD and AD patients, respectively. The area under the ROC curve (AUC) was 0.944±0.0219, indicating high accuracy, 0.877-0.981 of 95% confidence interval (CI) and 20.271 of z statistic (P<0.0001), indicated the sensitivity of about 86.4% and the specificity of 90.6% as shown in FIG. 2(B).

Figure 3:
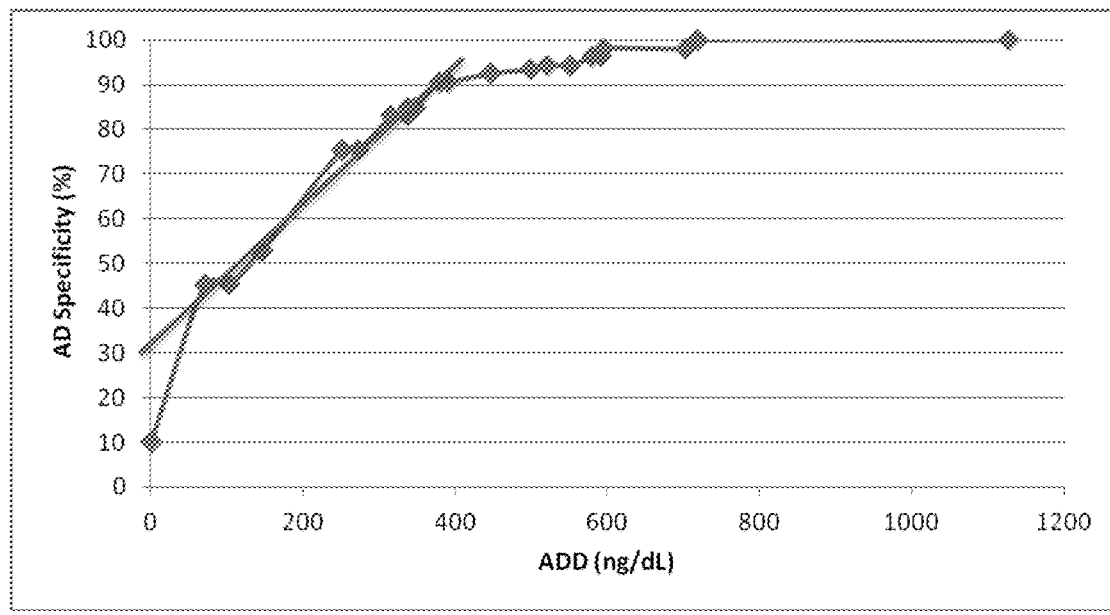
FIG. 3 provides a ROC curve as plotted according to the statistic data of specificity (%) as Y-axis, and the levels of GAPDH in a plasma sample (ADD) as X-axis.
Figure 4:
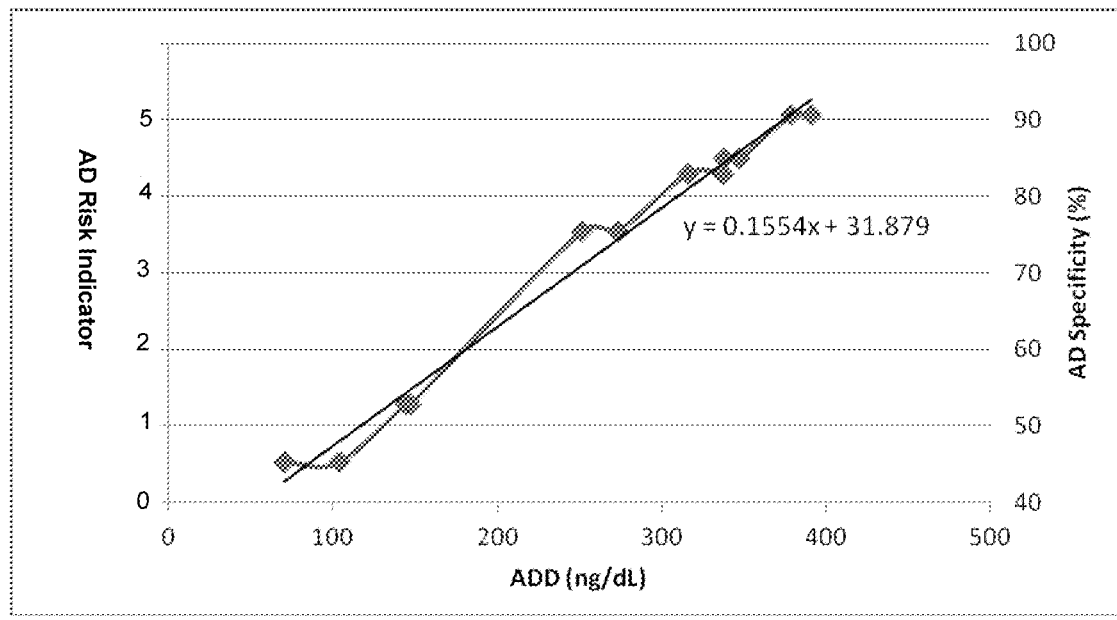
FIG. 4 provides a regression line taken from the ROC curve given in FIG. 3.

Furthermore, the receiver operating characteristic curve (ROC curve) was obtained according to the statistic data of specificity (%) as Y-axis, and the GAPDH levels in plasma samples as X-axis. The ROC curve was plotted as FIG. 3. Taken from the linear portion of the ROC curve given in FIG. 3, a regression line, y=0.1554x+31.879, was obtained, see FIG. 4, which is divided by 5 grades of AD Risk indicators. The meanings of the 5 grades of AD Risk indicators are given in Table 2.

TABLE 2

Meanings of 5 grades according to the method of the invention

| AD Risk Indicator | Meanings |
|---|---|
| >5 | Strong evidence to rule in Alzheimer's disease |
| 4~5 | Moderate evidence to rule in Alzheimer's disease |
| 3~4 | Weak evidence to rule in Alzheimer's disease |
| 2~3 | Weak evidence to rule out Alzheimer's disease |
| 1~2 | Moderate evidence to rule out Alzheimer's disease |
| <1 | Strong evidence to rule out Alzheimer's disease |

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

We claim:

1. A method for diagnosis and treatment of Alzheimer's disease (AD) in a subject, comprising the steps of:
   (1) obtaining a sample from said subject, wherein the subject's sample is a urine or saliva sample;
   (2) measuring only the levels of glyceraldehyde 3-phosphate dehydrogenase (GAPDH) protein in the subject's sample;
   (3) based upon the level of GAPDH in the subject's sample as measured in step (2), diagnosing the subject with AD by comparing the level of GAPDH protein in the subject's sample to an AD reference that refers to the level of GAPDH protein about 720 ng/dL,
   wherein the AD reference is independent of age and sex,
   wherein the level of GAPDH protein in the subject's sample higher than 720 ng/dL is indicative of AD in the subject; and
   (4) administering a treatment for AD to the subject.

* * * * *